United States Patent
Veittinger

(10) Patent No.: US 10,369,673 B2
(45) Date of Patent: Aug. 6, 2019

(54) SPINDLE DEVICE FOR A PROGRAM-CONTROLLED MACHINE TOOL

(71) Applicant: DECKEL MAHO PFRONTEN GMBH, Pfronten (DE)

(72) Inventor: Hans Veittinger, Kempten (DE)

(73) Assignee: DECKEL MAHO PFRONTEN GMBH, Pfronten (DE)

(*) Notice: Subject to any disclaimer, the term of this patent is extended or adjusted under 35 U.S.C. 154(b) by 0 days.

(21) Appl. No.: 15/548,276

(22) PCT Filed: Feb. 2, 2016

(86) PCT No.: PCT/EP2016/052203
§ 371 (c)(1),
(2) Date: Aug. 2, 2017

(87) PCT Pub. No.: WO2016/124609
PCT Pub. Date: Aug. 11, 2016

(65) Prior Publication Data
US 2018/0021908 A1   Jan. 25, 2018

(30) Foreign Application Priority Data
Feb. 2, 2015 (DE) .................... 20 2015 001 082 U

(51) Int. Cl.
*B24B 41/04* (2006.01)
*B23Q 17/12* (2006.01)
(Continued)

(52) U.S. Cl.
CPC .............. *B23Q 17/12* (2013.01); *B23Q 1/70* (2013.01); *B23Q 3/12* (2013.01); *B23Q 5/043* (2013.01);
(Continued)

(58) Field of Classification Search
CPC . B23Q 17/12; B23Q 1/70; B23Q 3/12; B23Q 5/043; B23Q 17/0971;
(Continued)

(56) References Cited

U.S. PATENT DOCUMENTS 4,744,348 A * 5/1988 Oda ........................ B24B 47/22
125/11.03
5,168,758 A   12/1992 Wolfer
(Continued)

FOREIGN PATENT DOCUMENTS

CN   103 967 942 A    8/2014
DE    36 27 796 C1   10/1987
(Continued)

OTHER PUBLICATIONS

May 10, 2016 Search Report issued in International Patent Application No. PCT/EP2016/052203.
(Continued)

*Primary Examiner* — George B Nguyen
(74) *Attorney, Agent, or Firm* — Oliff PLC

(57) ABSTRACT

A machining unit for a program-controlled machine tool. In particular, a spindle device for a program-controlled machine tool including a spindle housing; a working spindle which is mounted in the spindle housing in a rotatable manner about a spindle axis and which includes a clamping device for clamping a tool interface that is inserted in a tool receiving section of the spindle device and is configured to hold a milling or boring tool; and a sensor device which is arranged on the spindle housing and which includes at least one structure-borne sound sensor configured to detect structure-borne sounds or vibrations occurring during grinding operations.

15 Claims, 6 Drawing Sheets

(51) Int. Cl.
  *B23Q 1/70* (2006.01)
  *B23Q 17/09* (2006.01)
  *B23Q 17/22* (2006.01)
  *B24B 49/00* (2012.01)
  *G01N 29/14* (2006.01)
  *B23Q 3/12* (2006.01)
  *B23Q 5/04* (2006.01)

(52) U.S. Cl.
  CPC ..... *B23Q 17/0971* (2013.01); *B23Q 17/2241* (2013.01); *B24B 41/04* (2013.01); *B24B 49/003* (2013.01); *G01N 29/14* (2013.01); *B23Q 2220/006* (2013.01); *B23Q 2717/00* (2013.01)

(58) Field of Classification Search
  CPC .......... B23Q 17/2241; B23Q 2220/006; B23Q 2717/00; B24B 41/04; B24B 49/003; B24B 53/08
  USPC .............................................. 451/443, 56, 8
  See application file for complete search history.

(56) References Cited

U.S. PATENT DOCUMENTS

| | | | |
|---|---|---|---|
| 5,618,993 A | | 4/1997 | Matsumoto et al. |
| 5,624,365 A | * | 4/1997 | Haninger ............. B23Q 3/1554 483/38 |
| 5,662,567 A | * | 9/1997 | Rutschle ................ B23B 31/00 408/239 R |
| 6,038,948 A | * | 3/2000 | Link ..................... B23B 31/302 279/114 |
| 6,217,420 B1 | * | 4/2001 | Stocker .................. B23Q 3/186 257/E21.23 |
| 6,290,574 B1 | * | 9/2001 | Thyssen .............. B23F 23/1225 451/10 |
| 9,314,891 B2 | * | 4/2016 | Veittinger ............. B23Q 17/002 |
| 2002/0017139 A1 | * | 2/2002 | Kluft .................. G05B 19/4065 73/593 |
| 2009/0116775 A1 | | 5/2009 | Oguma et al. |
| 2011/0209546 A1 | * | 9/2011 | Seuthe ............... B23Q 17/0976 73/579 |
| 2014/0212236 A1 | | 7/2014 | Veittinger |
| 2015/0258650 A1 | * | 9/2015 | Okamoto ........... B23Q 17/2241 381/56 |
| 2016/0199963 A1 | * | 7/2016 | Ribbeck ................. B24B 49/14 451/5 |

FOREIGN PATENT DOCUMENTS

| | | |
|---|---|---|
| DE | 196 26 879 A1 | 1/1998 |
| DE | 10 2013 201 328 A1 | 7/2014 |
| EP | 0 459 948 A2 | 12/1991 |
| EP | 1 927 855 A1 | 6/2008 |
| JP | S62-114854 A | 5/1987 |
| JP | S62-242853 A | 10/1987 |
| JP | H09-196751 A | 7/1997 |
| JP | 2015-000436 A | 1/2015 |

OTHER PUBLICATIONS

May 10, 2016 Written Opinion issued in International Patent Application No. PCT/EP2016/052203.

Aug. 21, 2018 Office Action issued in Chinese Patent Application No. 201680008459.3.

Nov. 7, 2018 Office Action issued in Japanese Patent Application No. 2017-540740.

\* cited by examiner

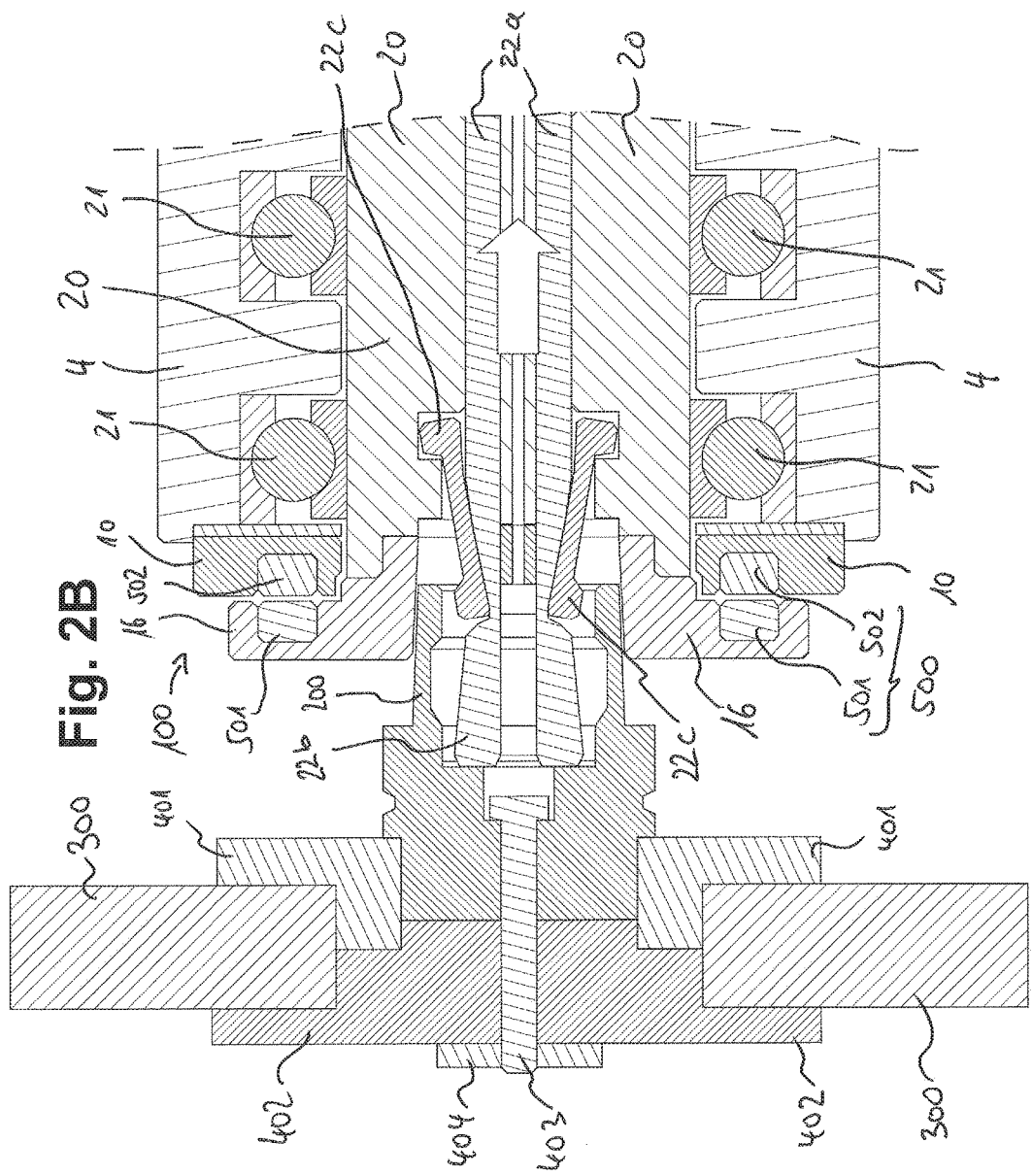

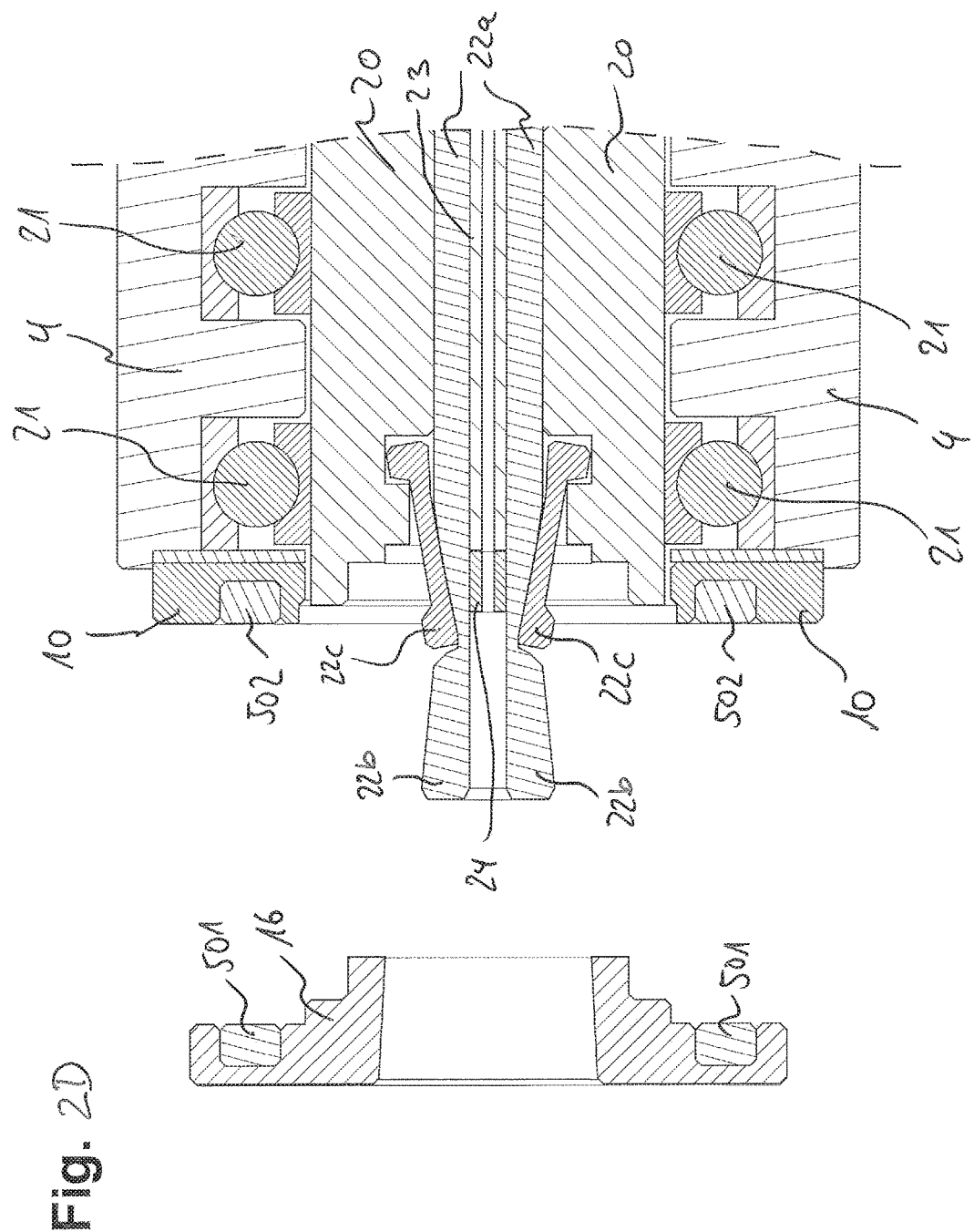

SPINDLE DEVICE FOR A PROGRAM-CONTROLLED MACHINE TOOL

The present invention relates to a machining unit, in particular a working spindle, for a program-controlled machine tool or a spindle device for a program-controlled machine tool, in particular for a milling machine, a milling/lathing machine, a universal milling machine, a universal machine tool or a CNC machining centre.

BACKGROUND

For the machining and/or manufacturing of workpieces, machine tools which can be universally used, in particular program-controlled or numerically controllable machine tools, are known in the prior art, e.g., milling machines, universal milling machines, universal machine tools and/or CNC machining centres, which usually include one or more tool-carrying working spindles for receiving, e.g., drilling and milling tools.

On such tool-carrying working spindles, tools can be received with tool interfaces such as tool tapers, in particular Morse tapers, steep tapers, or hollow shank tapers, on receiving devices or tool receptacles of the working spindles, in order to then be driven on the working spindle. These can be various drilling or milling tools or other tools which are respectively clamped or fixed to the typically standardized tool interfaces.

However, in accordance with today's multi-layered requirements in the manufacturing of workpieces, it may also be advantageous to also perform, instead of or in addition to the conventional milling or drilling tools for milling or drilling operations on a workpiece on the universally applicable machine tool, additional or alternative grinding operations on the workpiece at the universally applicable machine tool, for which usually special program-controlled grinding machines are provided so that the workpiece usually has to be clamped on the special program-controlled grinding machine for grinding operations after milling or drilling operations on the universally applicable machine tool or the workpiece usually has to be clamped usually on a milling machine or a universally applicable program-controlled machine tool for milling or Drilling operations after grinding operations on the special program-controlled grinding machine.

In view of the above considerations or problems, an object of the invention is to develop or provide a universally applicable program-controlled tool machine in such a way that it also allows, in addition to the usual milling and drilling operations on a workpiece, efficient, accurate and reliable grinding operations, in particular, for example, when using a grinding tool on the universally applicable program-controlled machine tool, which is usually configured for milling and drilling operations; on the one hand, preferably without limiting the universal machining options of the milling and drilling operations, but preferably still ensuring today's requirements for precision, efficiency and reliability of the grinding operations, e.g., similar or even better in comparison to the efficiency, precision and reliability achievable on the prior art special program-controlled grinding machines.

A machining unit of the generic kind is known, e.g., from DE 10 2013 201 328 A1, in which sensor system for use in milling and drilling operations may be accommodated on an end face of a working spindle of a machine tool.

SUMMARY

In view of the above-mentioned object of the invention, a spindle device for use on a program-controlled machine tool according to claim 1 or a corresponding machining unit with a working spindle for a program-controlled machine tool is proposed according to the invention, and, according to an independent claim, also a program-controlled machine tool is proposed, comprising a plurality of such spindle devices according to the invention for use on the program-controlled machine tool or one or more such corresponding machining units with a working spindle for the program-controlled machine tool. Dependent claims relate to preferred embodiments of the invention.

According to the invention, a spindle device for a program-controlled machine tool is proposed, comprising a spindle housing, a working spindle rotatably mounted about a spindle axis in the spindle housing which comprises a clamping device for clamping a tool interface inserted in a tool receiving portion of the spindle device and adapted to hold a milling or drilling tool, and a sensor device arranged on the spindle housing and including at least one structure-borne sound sensor configured to detect structure-borne sound waves or vibrations occurring during grinding operations.

In particularly preferred and advantageous embodiments, the structure-borne sound sensor is configured as an annular (or at least partially annular) structure-borne sound sensor.

Preferably, the annular structure-borne sound sensor comprises an annular (or at least partially annular) rotor sensor portion and/or an annular (or at least partially annular) stator sensor portion.

In particularly preferred and advantageous embodiments, a first ring element and a second ring element may be provided, wherein the first ring element may preferably be fixedly connected to the spindle housing and/or the second ring element may preferably be fixedly connected to the rotatably mounted working spindle. Preferably, at least a portion of the structure-borne sound sensor may be arranged or held at least on or in one of the first and second ring elements.

Preferably, the annular rotor sensor portion is disposed or held in or on the second ring element, and/or preferably the annular stator sensor portion is disposed or held in or on the first ring element.

Preferably, the second ring element is connected, preferably in a rotationally fixed manner, to a spindle head shank of the spindle device, which is preferably rotatably mounted in the spindle housing, or is fastened thereto, in particular preferably detachably fastened.

In particularly preferred and advantageous embodiments, an inner portion of the second ring element forms at least a part of the tool receiving portion of the spindle device.

Preferably, the inner portion of the second ring element is in contact with at least a portion of the tool interface when the tool interface is inserted into the tool receiving portion of the spindle device and clamped by the clamping device. This has the advantage that the structure-borne sound can be guided from the tool interface to the ring element, on which or in which the structure-borne sound sensor may be arranged, in a particularly undisturbed manner.

Preferably, the first ring element is fastened to the spindle housing in a rotationally fixed manner, in particular preferably detachably fastened.

In particularly preferred and advantageous embodiments, the spindle device comprises a plurality of spindle bearings.

The structure-borne sound sensor is preferably arranged on a side of the outermost spindle bearing of the plurality of spindle bearings which faces the outer side of the spindle device. Particularly preferably, the structure-borne sound sensor is positioned such that none of the spindle bearings is located in a direct propagation direction of structure-borne sound waves in the spindle device from the tool receiving portion toward the structure-borne sound sensor.

In further exemplary aspects, the spindle device or the structure-borne sound sensor thereof may be calibrated by means of an additional (e.g., conventional) structure-borne sound sensor, e.g., by detecting the touch of the grinding tool through a second structure-borne sound sensor in addition to the structure-borne sound sensor of the spindle device and comparing the signals of the sensors for the calibration of the structure-borne sound sensor of the spindle device. In further exemplary aspects, the spindle device and its structure-borne sound sensor may be calibrated by means of an additional (e.g., conventional) structure-borne sound sensor, e.g., by attaching a second structure-borne sound sensor to a workpiece to be machined or to workpiece clamping means of the machine tool and comparing the signals of the sensors, e.g., during machining or test machining of a test work piece, for the calibration of the structure-borne sound sensor of the spindle device.

In further exemplary aspects, preferably a method of grindingly machining a workpiece on a universally applicable machine tool with a spindle device described above may be provided, comprising: grindingly machining a workpiece clamped on a workpiece clamping means of the machine tool using a grinding tool which is held on a tool interface which is clamped on the clamping device of the working spindle of the spindle device and is inserted into the tool receiving portion of the spindle device, and detecting the structure-borne sound waves or vibrations occurring during the grinding operations by means of the structure-borne sound sensor of the sensor device of the spindle device.

In further exemplary aspects, preferably a method of dressing a grinding tool on a universally applicable machine tool with a spindle device described above may be provided, comprising: performing a dressing operation for a grinding tool which is held on a tool interface which is clamped on the clamping device of the working spindle of the spindle device and is inserted into the tool receiving portion of the spindle device, on a dressing piece while monitoring the dressing operation on the basis of a structure-borne sound signal of the structure-borne sound sensor of the sensor device of the spindle device.

BRIEF DESCRIPTION OF THE FIGURES

FIGS. 2A, 2B, 2C and 2D show exemplary schematic sectional views or partial sectional views of a machining unit for a program-controlled machine tool according to a further exemplary embodiment of the present invention.

DETAILED DESCRIPTION OF THE FIGURES AND EXEMPLARY EMBODIMENTS

In the following, examples of the present invention will be described in detail with reference to the accompanying figures. The same or similar elements in the figures may be designated with the same reference signs, but sometimes also with different reference signs.

It should be emphasized, however, that the present invention is in no way limited or restricted to the exemplary embodiments described in the following and to the embodiments thereof, but also comprises modifications of the exemplary embodiments, in particular those which are encompassed by modifications of the features of the described examples or by the combination of individual or a plurality of the features of the described examples within the scope of the independent claims.

Figure 1:
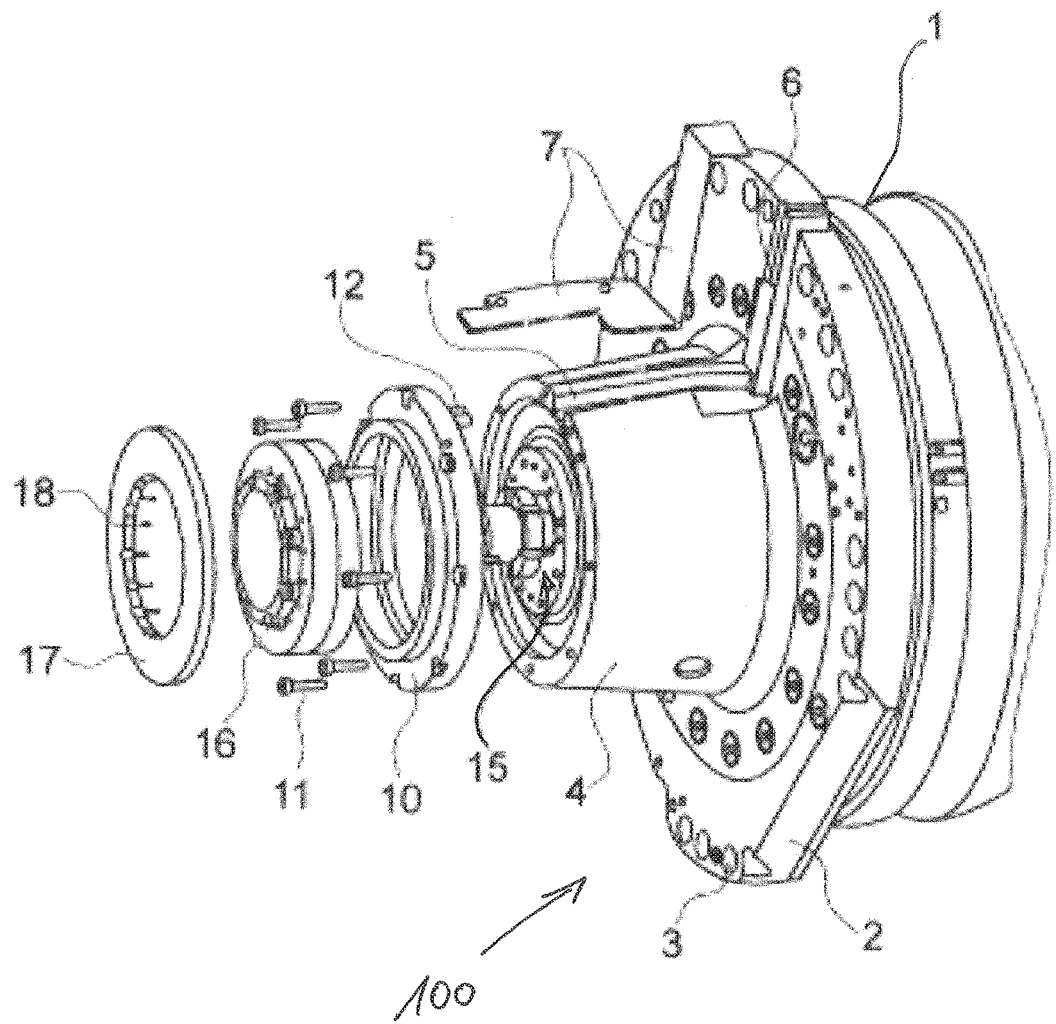
FIG. 1 shows an exemplary schematic perspective exploded view of a machining unit for a program-controlled machine tool according to an exemplary embodiment of the present invention.

FIG. 1 shows an exemplary schematic perspective exploded view of a machining unit for a program-controlled machine tool according to an exemplary embodiment of the present invention.

In particular, FIG. 1 shows an exemplary schematic perspective exploded view of parts of a spindle device 100 of a working spindle, in particular a tool-carrying working spindle, for a program-controlled machine tool (not shown) according to an exemplary embodiment of the present invention.

The exemplary machining unit illustrated including a working spindle or spindle device 100 is, for example, configured to perform milling and/or drilling operations on workpieces which are clamped on workpiece clamping means of the machine tool, e.g., by means of tools, in particular milling and drilling tools, which are not shown in FIG. 1 and which can usually be clamped on the working spindle or spindle device using tool interfaces which can be exchanged at the working spindle and are then rotationally driven by the working spindle or spindle device for generating or for driving the chipping movement at high rotational speeds.

One or more of the machining units including a working spindle or spindle devices 100 of a working spindle may, e.g., be provided for machining or manufacturing workpieces for or at machine tools, in particular, e.g., on program-controlled or numerically controllable machine tools, e.g., milling machines, milling/turning machines, universal milling machines, universal machine tools or CNC machining centres, which include one or more tool-carrying working spindles.

On such tool-carrying working spindles, tools can be received with tool interfaces such as tool tapers, in particular Morse tapers, steep tapers, or hollow shank tapers, on receiving devices or tool receptacles of the working spindles, in order to then be driven on the working spindle. These can be various drilling or milling tools or other tools which are respectively clamped or fixed to the typically standardized tool interfaces or tool tapers The machining unit or spindle device 100 according to FIG. 1 comprises, for example, a spindle housing 1, which may be attached to a further component of the machine tool or may be assembled therewith, in particular, by way of example, with a spindle head carrier or a swivel head of the machine tool and possibly with the aid of an annular flange 2, which, for example, has a plurality of axial bores 3 for fastening or assembling to/with further components of the machine tool. The working spindle 15 is rotatably mounted inside the housing 1.

A frustoconical housing part 4 of the machining unit or spindle device 100, in the circumferential wall of which an (or a plurality of) outwardly open longitudinal groove(s) 5 is incorporated, is fastened, for example, to the front side of the annular flange 2. The longitudinal groove 5 is continued, for example, in a receiving groove 6, which, for example, is formed in the annular flange 2. The longitudinal groove 5 and its continuation, i.e., for example, the receiving groove 6, form, for example, a receiving duct for a power and/or measurement data cable (not shown in FIG. 1) which is guided in this receiving duct 5, 6 and may then be covered by a shaped plate 7 detachably fastened to the housing part 4.

In FIG. 1, a first ring element 10, which, for example, may be detachably fastened to the end face of the housing part 4 by a plurality of fasteners 11 (for example, bolts), is shown in front of the end face of the housing part 4. The first ring element 10 has, for example, a profiled cross-section and is, by way of example, supported on the left-hand annular end face of the housing part 4 by its right-hand end face (i.e., in particular by the side facing the spindle) or attached or detachably fastened thereto.

At the front end of the working spindle, a second ring element 16 is detachably fastened to the first ring element 10 by a plurality of fasteners (e.g., stud bolts), wherein the second ring element 16 co-rotates with the working spindle and may thus constitute a rotor.

The second ring element 16 has, for example, a cylindrical inner circumferential surface and, for example, a stepped cross-section. The second ring element 16 is covered by an annular cover element 17 which is detachably fastened to the, e.g., planar end surface of the spindle by means of fasteners (e.g., stud bolts 18) in planar contact and terminates the working spindle on the end face without covering the tool holder for clamping a tool shank.

Receiver and/or transmitter means, which may serve for the non-contact transmission of measurement data, sensor signals and/or power signals, may be accommodated in the first ring element 10, for example. Furthermore, a cable path portion 12, which is opposite the cable duct of the longitudinal groove 5 and which may project. In the assembled state, into this cable duct, is provided, for example, on the first ring element 10 for the electrical connection to the sensor system (e.g., a connection of the power cable and/or measurement cable to the receiver or transmitter means).

In the second ring element 10, one or more sensors may be accommodated. For example, this may be sensors, e.g., vibration sensors, by means of which operational deformations of the spindle or of the spindle head can be detected in the axial direction and also in the circumferential direction. Various types of sensors, for example, pressure-sensitive, voltage-sensitive, or force-sensitive sensors, are suitable as measuring sensors in order, for example, to detect alignment errors of the spindle and/or shape changes.

The sensor system optionally comprises an evaluation device, which is electronically coupled to the various sensors, which can evaluate and also store the acquired data, and which may be controlled by a microprocessor. By means of this sensor system, also the wear ratings of the cutting tools and possible damage to machine components caused by impact collisions may be detected, stored, and taken into account accordingly in the machine control system. Furthermore, using vibration sensors it is possible to carry out unbalance measurements or to detect bearing damage of bearings of the working spindle on the basis of an evaluation of the measurement signals.

The cable (measurement and/or power cable) guided in the cable duct 5 of the housing part 4 extends into the stationary outer ring (first ring element 10), which is fixedly connected to the spindle housing part 4. In this outer ring (first ring element 10), optionally connections for the power and measurement data cable are located, wherein this power or measurement cable may also be connected to a transmitter element arranged in the stationary outer ring (first ring element 10), the counterpart (receiver element) of which may be located in the rotor ring (second ring element 16) co-rotating with the spindle.

According to the exemplary embodiment of the invention, the spindle device 100 is configured to allow for grinding operations, wherein a grinding tool attached or clamped to the tool interface, e.g., a grinding wheel attached or clamped to the tool interface for planar and/or longitudinal grinding of a tool, is inserted instead of a milling or drilling tool by means of the coupleable tool interface.

For machining a workpiece with a grinding tool inserted or replaced on the spindle device 100, the sensor system of the spindle device is configured such that the sensors or the sensor system of the spindle device 100 comprises at least one structure-borne sound sensor configured to detect sound of structure-borne sound which is caused or produced during the grinding operation on the workpiece and is transmitted to the elements or components of the spindle device 100 via the grinding tool and the tool interface.

As background, it should be pointed out that the term "structure-borne sound" (or acoustic emission or "AE") describes a propagation of structure-borne sound waves or vibrations in a solid, wherein a propagation of longitudinal waves or vibrations (in particular, waves or vibrations in the internal structure of the solid) and/or a propagation of transverse waves or vibrations (in particular, waves or vibrations on the surface of the solid) may occur in the solid, usually at different propagation speeds (structure-borne sound speeds).

For example, structure-borne sound waves occur typically at frequencies in the ultrasonic range, and particularly at about 20 kHz to 2 MHz, and thus typically outside the frequency range of human audibility. For example, the propagation speed in steel is about 5000 m/s for longitudinal waves or vibrations and about 3100 m/s for transversal waves or vibrations.

Typical measuring ranges of structure-borne sound sensors are, e.g., in the range of 50-900 kHz, or preferably in the range of 100-400 kHz, particularly to reduce resonance effects.

Particularly in the case of grinding operations (i.e., cutting process with a geometrically undefined cutting edge, as opposed to the cutting process with a geometrically defined cutting edge, e.g., milling or drilling), typically structure-borne sound occurs which is produced at the workpiece when it is in contact with the grinding tool during the cutting process, then spreads in the workpiece and in the grinding tool and is transmitted to further connected elements.

Such vibrations can be detected sensorically by means of structure-borne sound sensors and thus can already provide information about the cutting process with a geometrically undefined cutting edge during the machining process so that the structure-borne sound measurement by means of diagnostic units and data monitoring units of the evaluation units or the machine control allow for instant monitoring or process monitoring of the machining operation and the process parameters during the grinding process.

For grinding operations, it is, e.g., possible to detect or sense, on the basis of the monitoring of the structure-borne sound signal during the machining or during the dressing operation, when/if, during the displacement of the grinding tool (with a geometrically undefined cutting edge) towards the workpiece to be machined and/or the displacement of the workpiece towards the grinding tool a first contact is made between the grinding tool or the first abrasive grains of the grinding tool surface and the workpiece surface (so-called first-cut detection).

This is also advantageous in a dressing operation on the grinding tool (which usually has to be carried out on special dressing devices), in particular, because it is possible, on the basis of the monitoring of the structure-borne sound signal during the dressing process, to detect or sense when/if during the displacement of the grinding tool (with a geometrically undefined cutting edge) towards the dressing piece (e.g., dressing diamond) and/or during the displacement of the dressing piece towards the grinding tool a first contact between the grinding tool or the first abrasive grains of the grinding tool surface with the surface of the dressing piece is made.

For example, in addition to the detection of a first contact on the basis of the structure-borne sound signal, during the dressing process also the further advantageous option of detecting, on the basis of the structure-borne sound signal, when the dressing operation can be terminated; e.g., when a grinding surface of the grinding tool is completely dressed, is provided, since this can be detected or sensed by a continuous structure-borne sound signal.

Herein, the machine control of the machine tool may optionally have an automatic program cycle which the operator can easily start, wherein, for example, during the dressing process, an automatic approach can be carried out with larger spacing steps in a first automatic cycle step until the first contact is detected at the machine control on the basis of the structure-borne sound signal, in order to then automatically carry out the actual dressing process in smaller spacing steps, until, on the basis of a continuous structure-borne sound signal detected at the machine control, it is recognized that the dressing process can be terminated, whereupon the machine control terminates the automatic cycle, and the operator is informed via the user interface that the automatic dressing operation has been terminated.

During the actual approach of the grinding tool towards the workpiece to be machined during the machining operation, it is also conceivable that an automatic delivery cycle is stored at the machine control of the machine tool, which the machine control can perform automatically for the approach operation in a program-controlled manner. In this case, it is advantageous that the workpiece and the grinding tool can be moved relative to one another without optical control by the operator, wherein in a first automatic cycle step in rapid traverse, i.e., at high displacement speeds of one or more linear or circular axes of the machine tool, they are automatically moved to a safety position (e.g., a preset safety distance) in order to then, in a second automatic cycle step of the approach operation, be moved by means of an automatic approach with small spacing steps (air grinding), until the first contact is detected on the basis of the structure-borne sound signal at the machine control, whereupon the actual program-controlled machining operation is started, e.g., either automatically or via a manual start command by the operator.

The actual grinding operation can be terminated automatically if the machine control recognizes on the basis of a detected continuous structure-borne sound signal that the machining operation can be terminated, since a desired surface characteristic of the ground workpiece is obtained ("component completely ground"), whereupon the machine control terminates the automatic machining operation, and the operator is informed by the user interface that the automatic machining operation is terminated.

Furthermore, the structure-borne sound signal output from the structure-borne sound sensor may additionally be used for collision monitoring (no additional collision sensor required), for undersize detection (a workpiece with undersize which is too small), for discarding the workpiece with undersize, and/or for process visualization (e.g., for the subsequent process analysis or error analysis). In preferred embodiments, the structure-borne sound sensor signal of the structure-borne sound sensor and/or one or more evaluation parameters based on the evaluation of the structure-borne sound signal may be displayed or illustrated on the operating interface or user interface of the numerical control of the machine tool or on a monitor of a control console of the machine tool.

In the preferred embodiment according to FIG. 1, a structure-borne sound sensor is provided on the spindle device 100, which, in particular, may preferably be configured as an annular structure-borne sound sensor.

This has the advantage that during the grinding operation, when a grinding tool with a tool interface is exchanged or received on the spindle device 100, by means of the enabled structure-borne sound measurement or detection, a grinding operation can be carried out, in which the detected structure-borne sound signal can advantageously be used, for example, for the grinding process or the monitoring thereof, for first-cut detection or sensing the first contact, for the dressing or truing process (optionally according to the above-described automatic program cycle) and/or for the automatic approach or adjustment of the grinding tool relative to the workpiece (optionally according to the automatic program cycle described above). Thus, even on universally applicable machine tools with a tool-carrying working spindle, which are usually provided for milling and drilling operations, an additional grinding operation is advantageously made possible, in which the necessary processes for the grinding operation can be performed easily, reliably, safely, automatically or semi-automatically and with high accuracy and efficiency.

However, no restrictions in the functionalities for the milling and drilling operations emerge in the case of the additional provision of the structure-borne sound sensor on the working spindle of the universally applicable machine tool, which is usually used for milling and drilling operations, so that an exclusively advantageous further development of the universally applicable machine tool and its possible applications is provided. On the contrary, even synergy effects arise because the structure-borne sound sensor can also be used in milling and drilling operations, e.g., to detect bearing damage on the spindle, or for collision detection. Thus, for example, in exemplary embodiments it is even possible to omit other collision sensors or vibration sensors which are usually required.

In the exemplary embodiment according to FIG. 1, preferably an annular structure-borne sound sensor is installed, which includes a preferably annular (or preferably at least partially annular) rotor sensor portion and a preferably annular (or preferably at least partially annular) stator sensor portion, wherein the rotor sensor portion is preferably arranged, attached and/or integrated on the outer second ring element 16, and/or wherein the rotor sensor portion is preferably arranged, attached and/or integrated on the inner first ring element.

Herein, the stator sensor portion and the rotor sensor portion are preferably arranged in such a way that an air gap is formed between the stationary stator sensor portion and the rotatable rotor sensor portion, wherein sensor signals are transmitted without contact between the stator sensor portion and the rotor sensor portion.

FIGS. 2A, 2B, 2C and 2D show exemplary schematic sectional views or partial sectional view of a machining unit for a program-controlled machine tool according to a further exemplary embodiment of the present invention.

In particular, FIGS. 2A to 2D are exemplary schematic partial sectional views of parts of a spindle device 100 of a working spindle, in particular a tool-carrying working spindle, for a program-controlled machine tool (not shown) according to an exemplary embodiment of the present invention.

The spindle device 100 according to the exemplary embodiment according to FIGS. 2A to 2D includes, by way of example, a spindle housing element 4 of the spindle housing of the working spindle. In the interior of the spindle housing element 4, for example, a spindle head shank 20 of the working spindle is mounted rotatably about the spindle axis by means of the bearing elements 21 (exemplarily shown as a ball bearing). The spindle head shank 20 is rotationally drivable via a spindle drive (not shown).

Furthermore, the spindle head shank 20 is configured, for example, as a hollow shank, in the inner section of which a clamping rod 22a of a clamping device for clamping tool interfaces is arranged, here, for example, for clamping a tool interface configured as a hollow shank taper 200. At one end portion of the clamping rod 22a on the side facing outwards from the spindle, the clamping rod 22a includes, for example, a clamping head 22b, which, for example, is formed integrally with the clamping rod 22a, but may also be attached to the clamping rod 22a as a separate part in further exemplary embodiments. Furthermore, the clamping device comprises a plurality of clamping chuck elements 22c configured to clamp a tool taper (here, for example, a hollow shank taper 200) when the clamping rod 22a is pulled inside the spindle in the spindle axis direction for clamping the tool taper.

Figure 2A:
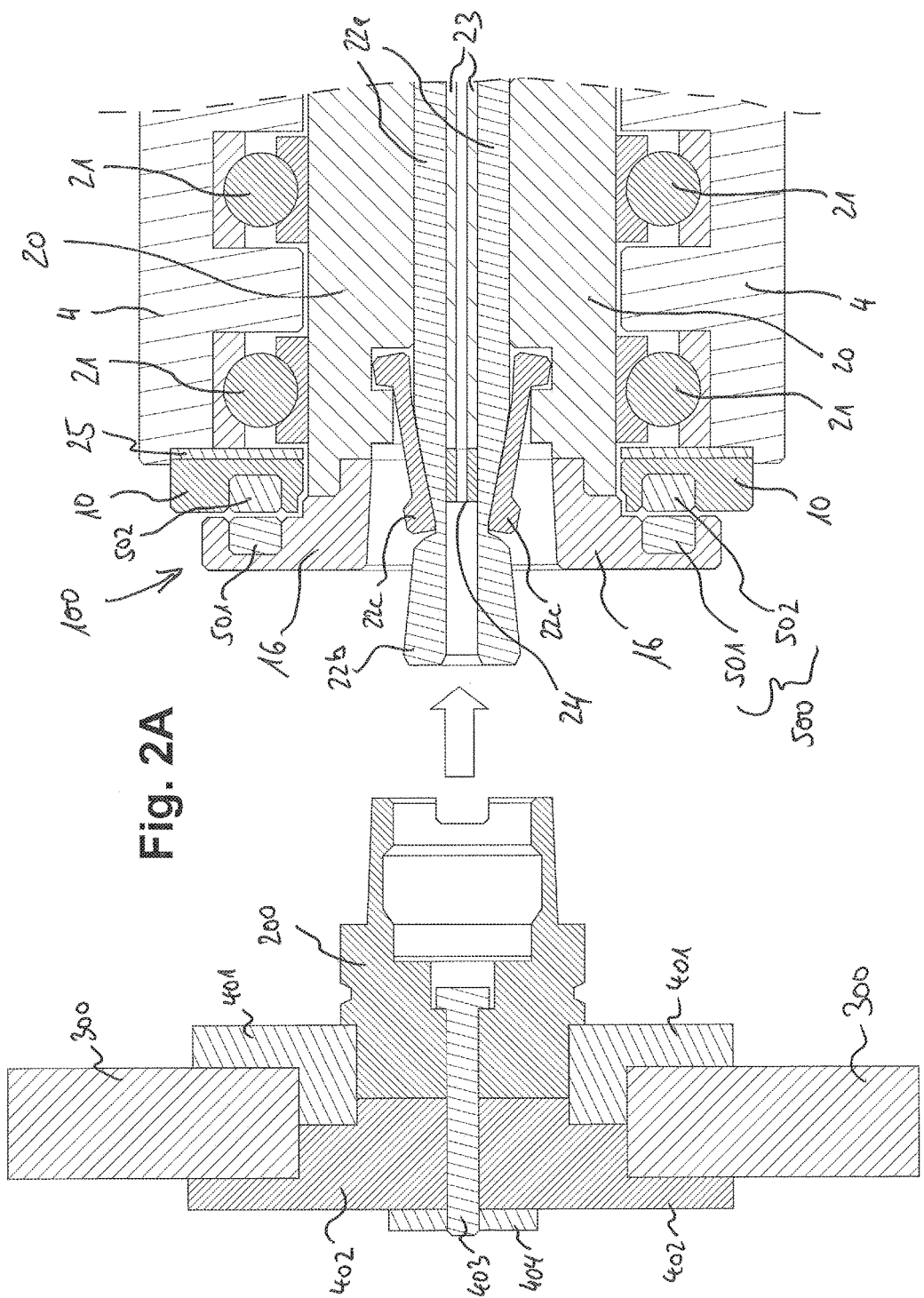
Figure 2C:
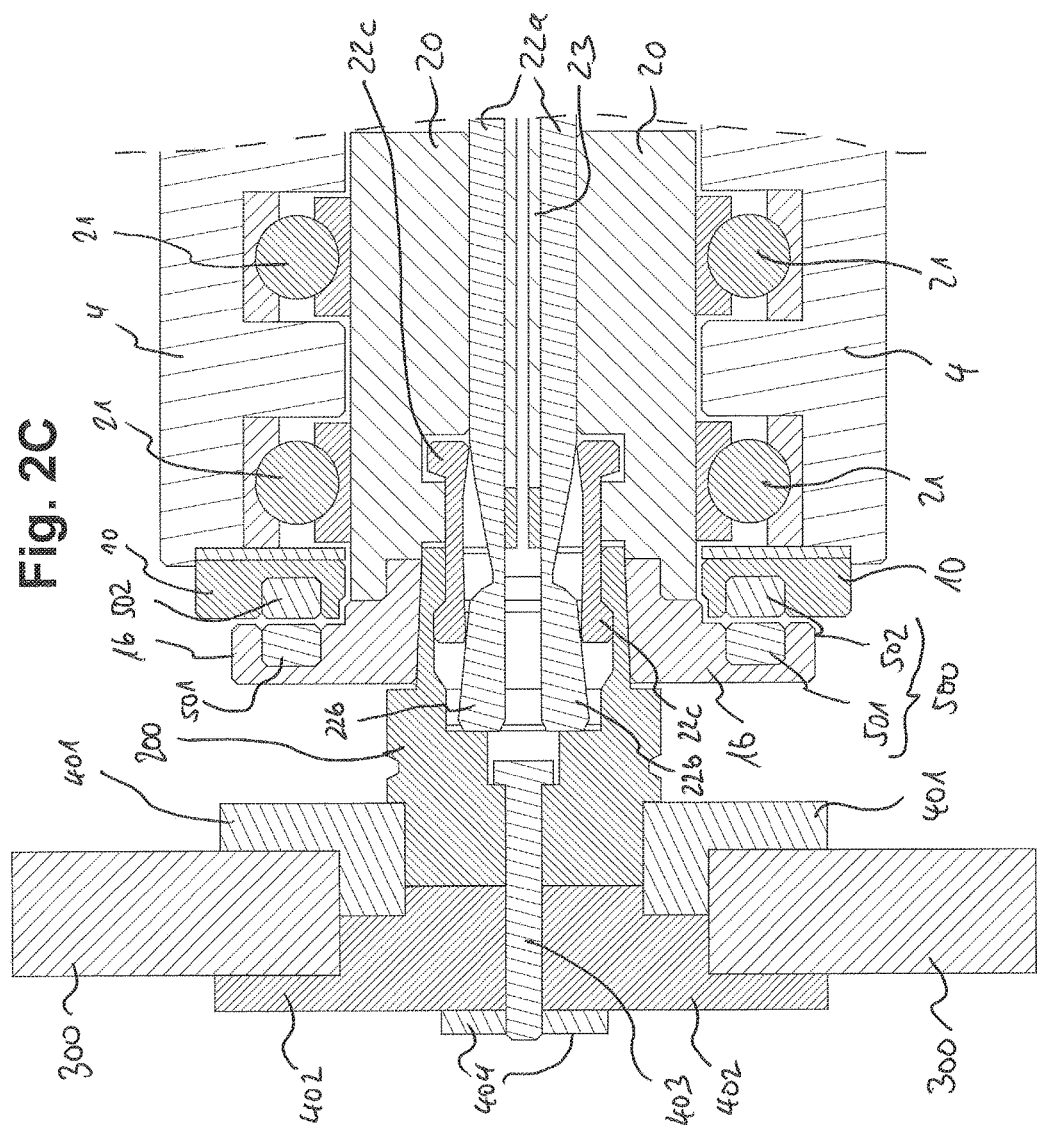

This is particularly shown or illustrated in the summary view of FIGS. 2A to 2B, wherein the hollow shank taper 200 in the unclamped state, i.e., when the clamping rod 22a is extended in the direction of the arrow in FIG. 2A, can be inserted into a tool receptacle formed on the working spindle or attached to the clamping head 22b (FIG. 2B), and can then, when the clamping rod 22a with the clamping head 22b is retracted in the direction of the spindle axis, i.e., in the direction of the arrow in FIG. 2B, into the interior of the spindle, the hollow shank taper 200 is clamped by means of the clamping chuck elements 22c forced apart by the clamping head 22b (FIG. 2C).

For example, a supply pipe element 23 (e.g., a tube, tubule, or hose) with a sealing element connected thereto is provided in the interior of the axially hollow clamping chuck 22a, through which, in preferred embodiments, an internal cooling lubricant feed to the hollow shank taper 200 or optionally therethrough to the tool clamped or attached on the hollow shank taper 200 is provided.

Here, in FIGS. 2A to 2B, a grinding tool 300 (in particular, for example, a grinding wheel) is attached to the hollow shank taper 200 or fastened by means of the clamping elements 401 and 402 via the disk 404 and a fastener 403. Herein the attachment of the grinding tool 300 to the tool interface, i.e., to the exemplary hollow shank taper 200, is shown in a simplified manner only, and more complicated attachments, which are particularly equipped with further fastening mechanisms, are conceivable and advantageous. For example, the axial distance of the grinding wheel 300 to the body of the hollow shank taper 200 may also be increased by further intermediate elements in further exemplary embodiments.

According to the exemplary embodiment, the spindle device 100 further comprises a structure-borne sound sensor 500 arranged on the end face of the spindle device 100 for detecting a structure-borne sound signal on the basis of a structure-borne sound which propagates in the workpiece and the grinding tool 300 during the machining of a workpiece with the grinding tool 300 and is transmitted to elements and components of the spindle device 100 via the tool interface (e.g. the hollow shank taper 200).

Advantageously and exemplary, the structure-borne sound sensor 500 is configured as an annular structure-borne sound sensor 500 and comprises an exemplary annular rotor sensor portion 501 and an exemplary annular stator sensor portion 502.

The annular stator sensor portion 502 is arranged on an inner ring element 10 (first ring element), and the rotor sensor portion 501 is arranged on an outer ring element 16 (second ring element). Here, the annular stator sensor portion 502, the inner ring element 10, the rotor sensor portion 501, and the outer ring element 16 are axially aligned and axially centred on the spindle axis, wherein, in particular, the outer ring element 16 co-rotates with the rotor sensor portion 501 during the rotation of the spindle about the spindle axis.

On the end face, the inner ring element 10 is fastened to the spindle housing portion 4 or spindle housing element 4, in particular, preferably detachably fastened (for example, for simple replacement in case of maintenance, damage or wear or for repairing the sensor system).

On the end face, the outer ring element 16 is fastened to the spindle head shaft 20 and forms, as shown in FIGS. 2A to 2D, together with the end portion of the spindle head shaft 20, the tool receptacle or tool interface receptacle for receiving the tool interface, i.e., for example, for receiving a hollow shank taper 200 or other tool tapers, e.g., Morse tapers or steep tapers.

Herein, the stator sensor portion 502 and the rotor sensor portion 501, as well as the two ring elements 16 and 10, are arranged such that an air gap is formed between the stationary stator sensor portion 502 and the rotatable rotor sensor portion 501 or between the ring elements 10 and 16, wherein sensor signals are transmitted without contact between the stator sensor portion 502 and the rotor sensor portion 501.

The outer ring element 16 is, in particular, preferably detachably fastened (for example, for simple replacement in case of maintenance, damage or wear or for repairing the sensor system).

In this regard, FIG. 2D shows an exemplary situation in which the rotor sensor portion 501 of the structure-borne sound sensor 500, along with the outer ring element 16, is removed from the spindle device 100 or released from the attachment to the spindle device 100.

On the one hand, this allows the exchange or maintenance of the structure-borne sound sensor, but a further great advantage is that the outer ring element 10. and optionally also the inner ring element 16 act as additional dampening elements when, for example, unintended collisions occur at the working spindle of the machine tool, wherein, in the case of light to intermediate collisions, advantageously the ring elements, which are simple and inexpensive to replace, are damaged with the sensor system, instead of the possible occurrence of difficult or costly to repair damage even upon minor collisions at the working spindle, as is sometimes the case with conventional spindle devices.

Furthermore, one or more additional annular cover elements on the end face of the outer ring element 16 in further exemplary embodiments which are analogous to FIG. 1, as a result of which the dampening function is further enhanced, or a further disc element 25 arranged between the housing part 4 and the ring element 10 for further dampening may be provided.

Finally, it should be noted that the positioning of the structure-borne sound sensor 500 on the end face of the spindle or of the spindle housing 1 or 4 offers the advantage that the structure-borne sound waves or vibrations can be transmitted to the structure-borne sound sensor 500 virtually without interference via the received and clamped tool interface 200 and thus a detection of the structure-borne signal which is less susceptible to interference can be made possible.

Herein, positioning the structure-borne sound sensor 500 on a side of an outermost bearing or an outermost bearing element of the spindle facing the outside of the spindle is particularly advantageous, since positioning the structure-borne sound sensor 500 in the interior of the spindle can at least result in an undesirable disturbance of the structure-borne sound or vibrations to be detected, when the direction of propagation of the structure-borne sound waves from the tool interface to the position of the structure-borne sound sensor passes through or at least comes close to a bearing.

A particularly preferred embodiment is provided, in particular, when the tool receptacle is configured in such a way that the tool interface, in the clamped state, touches a ring element in the tool receptacle in which the rotor sensor portion 501 of the structure-borne sound sensor 500 is arranged, wherein, in particular, an inner portion of the ring element preferably forms at least one tool receiving portion of the spindle device or at least partakes in forming it.

Figure 3:
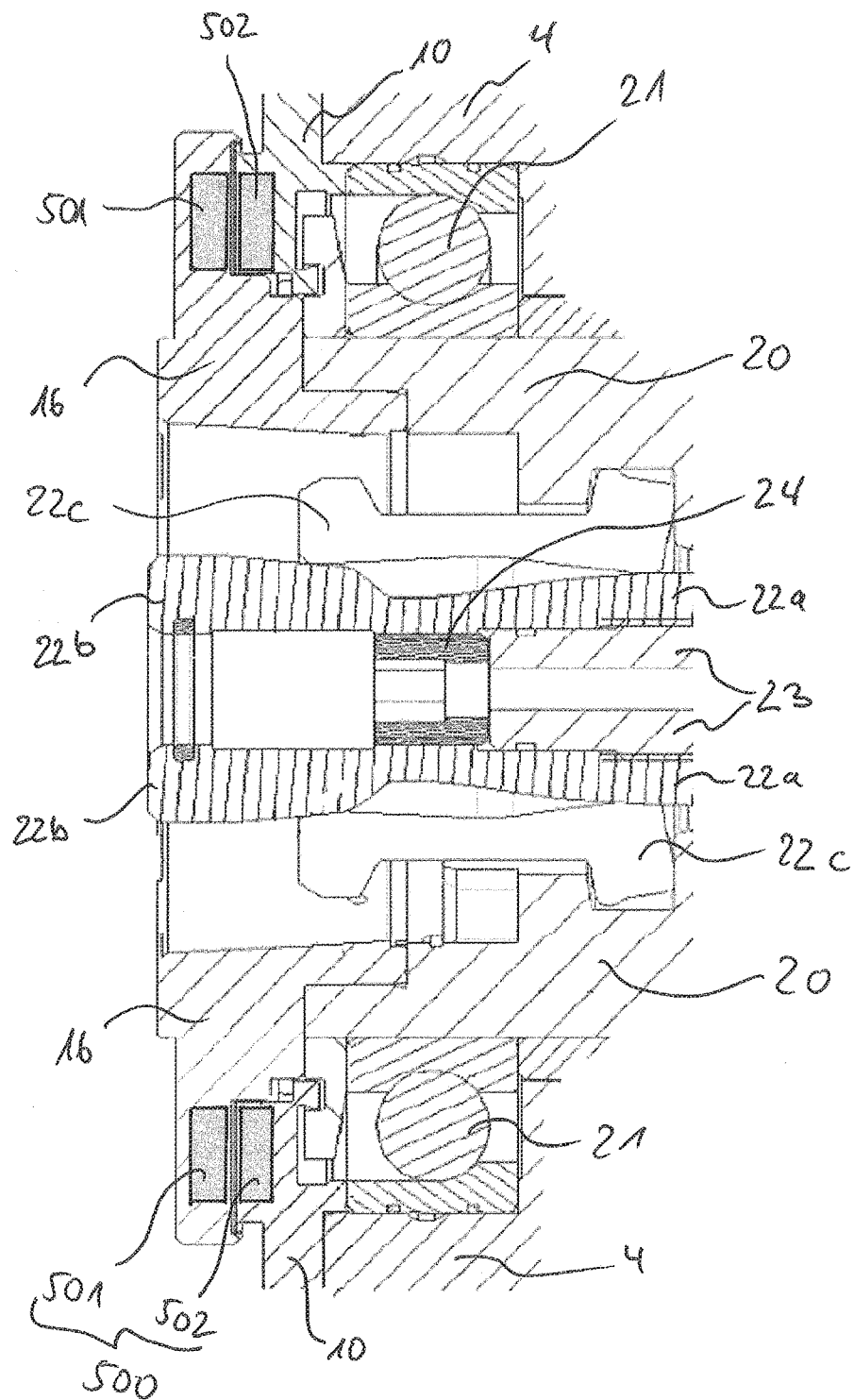
FIG. 3 shows an exemplary schematic sectional view or partial sectional view of a further machining unit for a program-controlled tool machine according to a further exemplary embodiment of the present invention.

FIG. 3 shows an exemplary schematic sectional view or partial sectional view of a further machining unit for a program-controlled machine tool according to a further exemplary embodiment of the present invention.

In particular, FIG. 3 shows an exemplary schematic partial sectional view of parts of a further spindle device 100 of a working spindle, in particular a tool-carrying working spindle, for a program-controlled machine tool (not shown) according to an exemplary embodiment of the present invention.

Herein, the components and elements of the spindle device 100 according to FIG. 3 are designated with the same reference signs as in the exemplary embodiments according to the exemplary embodiments described above, and differences essentially only exist in structural embodiments of the respective elements, so that here reference is made to the description of the figures, in particular of FIGS. 2A to 2C, which is essentially analogously valid for FIG. 3, in particular when the identical reference signs are taken into account.

The invention is not limited to the exemplary embodiments shown above but also extends to variants, modifications and combinations of the abovementioned features and exemplary embodiments. For example, the evaluation unit of the sensor system may be integrated functionally and/or also structurally into the inner ring, i.e., into the second ring element or into the rotor. However, the evaluation unit of the sensor system may also be arranged outside in an external component of the spindle or of the spindle housing and may be connected to the sensor system via a cable, and may optionally even be realized in the machine control.

The invention claimed is:

1. A spindle device for a program-controlled machine tool, comprising:
    a spindle housing,
    a working spindle rotatably mounted about a spindle axis in the spindle housing and comprising a clamping device for clamping a tool interface, which is inserted in a tool receiving portion of the spindle device and configured to hold a tool, and
    a sensor device arranged on the spindle housing at a front face of the working spindle and including at least one structure-borne sound sensor which is configured to detect structure-borne sound waves or vibrations occurring during grinding operations.

2. The spindle device according to claim 1, wherein
    the structure-borne sound sensor is configured as an annular structure-borne sound sensor.

3. The spindle device according to claim 2, wherein
    the annular structure-borne sound sensor comprises an annular rotor sensor portion and an annular stator sensor portion.

4. The spindle device according to claim 1, further comprising
    a first ring element and a second ring element, wherein the first ring element is fixedly connected to said spindle housing, and the second ring element is fixedly connected to the rotatably mounted working spindle, and at least a portion of the structure-borne sound sensor is arranged or held on or in at least one of the first and second ring elements.

5. The spindle device according to claim 4, wherein
    the annular rotor sensor portion is arranged or held in or on the second ring element, and/or
    the annular stator sensor portion is arranged or held in or on the first ring element.

6. The spindle device according to claim 4, wherein
    the second ring element is connected in a rotationally fixed manner to a spindle head shaft of the spindle device.

7. The spindle device according to claim 4, wherein
    an inner portion of the second ring element forms at least a part of the tool receiving portion of the spindle device.

8. The spindle device according to claim 7, wherein
    the inner portion of the second ring element is in contact with at least a portion of the tool interface when the tool interface is inserted in the tool receiving portion of the spindle device and is clamped by means of the clamping device.

9. The spindle device according to claim 4, wherein
    the first ring element is fastened to the spindle housing in a rotationally fixed manner.

10. The spindle device according to claim 1, further comprising
    a plurality of spindle bearings, wherein the structure-borne sound sensor is arranged on a side of the outermost spindle bearing of the plurality of spindle bearings which faces the outer side of the spindle device.

11. The spindle device according to claim 1, further comprising
    a plurality of spindle bearings, wherein the structure-borne sound sensor is positioned such that none of the spindle bearings is arranged in a direct propagation direction of structure-borne sound waves in the spindle device from the tool receiving portion toward the structure-borne sound sensor.

12. A method of grindingly machining a workpiece on a universally applicable machine tool with a spindle device according to claim 1, comprising:
    grindingly machining a workpiece clamped on a workpiece clamping means of the machine tool using a grinding tool which is held on a tool interface, which is clamped on the clamping device of the working spindle of the spindle device and is inserted in the tool receiving portion of the spindle device, and detecting the structure-borne sound waves or vibrations occurring during the grinding operations by means of the structure-borne sound sensor of the sensor device of the spindle device.

13. A method of dressing a grinding tool on a universally applicable machine tool with a spindle device according to claim 1, comprising:

performing a dressing operation for a grinding tool, which is held on a tool interface, which is clamped on the clamping device of the working spindle of the spindle device and is inserted in the tool receiving portion of the spindle device, on a dressing piece while monitoring the dressing operation on the basis of a structure-borne sound signal of the structure-borne sound sensor of the sensor device of the spindle device.

14. A spindle device for a program-controlled machine tool, comprising:

a spindle housing, a working spindle rotatably mounted about a spindle axis in the spindle housing and comprising a clamping device for clamping a tool interface, which is inserted in a tool receiving portion of the spindle device and configured to hold a tool, and a sensor device arranged on the spindle housing and including at least one structure-borne sound sensor which is configured to detect structure-borne sound waves or vibrations occurring during grinding operations, and the structure-borne sound sensor is configured as an annular structure-borne sound sensor.

15. A spindle device for a program-controlled machine tool, comprising:

a spindle housing, a working spindle rotatably mounted about a spindle axis in the spindle housing and comprising a clamping device for clamping a tool interface, which is inserted in a tool receiving portion of the spindle device and configured to hold a tool, a sensor device arranged on the spindle housing and including at least one structure-borne sound sensor which is configured to detect structure-borne sound waves or vibrations occurring during grinding operations, and a first ring element and a second ring element, wherein the first ring element is fixedly connected to said spindle housing, the second ring element is fixedly connected to the rotatably mounted working spindle, and at least a portion of the structure-borne sound sensor is arranged or held on or in at least one of the first and second ring elements, and an inner portion of the second ring element forms at least a part of the tool receiving portion of the spindle device.

* * * * *